(12) United States Patent
Lee

(10) Patent No.: US 10,076,548 B2
(45) Date of Patent: Sep. 18, 2018

(54) MIXTURE POWDERS OF PLATYCODON GRANDIFLORAS AND MOMORDICA CHARANTIA, AND METHOD FOR PRODUCING THE POWDERS

(71) Applicant: Kee Ho Lee, Yongin-si (KR)

(72) Inventor: Kee Ho Lee, Yongin-si (KR)

( * ) Notice: Subject to any disclaimer, the term of this patent is extended or adjusted under 35 U.S.C. 154(b) by 0 days.

(21) Appl. No.: 15/650,781

(22) Filed: Jul. 14, 2017

(65) Prior Publication Data

US 2018/0117107 A1    May 3, 2018

(30) Foreign Application Priority Data

Nov. 2, 2016    (KR) ........................ 10-2016-0145174

(51) Int. Cl.
| | | |
|---|---|---|
| *A61K 36/18* | (2006.01) | |
| *A61K 36/346* | (2006.01) | |
| *A61K 36/42* | (2006.01) | |
| *B01D 11/02* | (2006.01) | |

(52) U.S. Cl.
CPC ............ *A61K 36/18* (2013.01); *A61K 36/346* (2013.01); *A61K 36/42* (2013.01); *B01D 11/0292* (2013.01); *A61K 2236/51* (2013.01)

(58) Field of Classification Search
None
See application file for complete search history.

(56) References Cited

FOREIGN PATENT DOCUMENTS

| KR | 10-0862096 B1 | 10/2008 |
|---|---|---|
| KR | 10-1050821 B1 | 7/2011 |
| KR | 10-2013-0116500 A | 10/2013 |
| KR | 10-1312491 B1 | 10/2013 |

OTHER PUBLICATIONS

Zheng, et al., Plant Foods for Human Nutrition, 62:7. (Year: 2007).*
Sarkar, et al., Pharmacological Research, 33:1. (Year: 1996).*
Chungbuk National University Industry Cooperation Foundation, Development of Health Functional Food and Masspropagation of Adventitious Roots Using Bioreactor System in Tetraploid of Platycodon grandiflorum, Nov. 30, 2015, p. 1-262, 11-1543000-001021-01, Chungbuk National University Industry Cooperation Foundation, Cheongju-si, Chungcheongbuk-do, Republic of Korea.
Compendium of Herbal Medicine Textbook, Section II: Itemized Discussion, Pharmacognosy, Rev. 2, Feb. 25, 2014, p. 114, Dong Myeong Publishers, Paju-si, Gyeonggi-do, Republic of Korea.
Chang Ho Jeong and Ki Hwan Shim, Chemical Composition and Antioxidative Activities of Platycodon grandiflorum Leaves and Stems, Journal of the Korean Society of Food Science and Nutrition, Jun. 2006, p. 511-515, vol. 35, Issue 5, The Korean Society of Food Science and Nutrition, Busan-si, Republic of Korea.

* cited by examiner

*Primary Examiner* — Michael Barker
(74) *Attorney, Agent, or Firm* — KORUS Patent, LLC; Seong Il Jeong

(57) ABSTRACT

A method for preparing mixture powders of platycodon grandiflorus and momordica charantia includes washing at least one year-old platycodon grandiflorus, and momordica charantia wherein the platycodon grandiflorus includes stem, root, and leaf portions thereof; cutting the washed platycodon grandiflorus and momordica charantia; hot air-drying the cut platycodon grandiflorus and momordica charantia in a dryer at a temperature exceeding a boiling point of hydrogen cyanide gas to remove hydrogen cyanide therefrom; pulverizing the cut and dried platycodon grandiflorus and momordica charantia to prepare platycodon grandiflorus powders and momordica charantia powders; and mixing the platycodon grandiflorus powders and momordica charantia powders to produce the mixture powders of platycodon grandiflorus and momordica charantia.

2 Claims, 3 Drawing Sheets

MIXTURE POWDERS OF PLATYCODON GRANDIFLORAS AND MOMORDICA CHARANTIA, AND METHOD FOR PRODUCING THE POWDERS

CROSS-REFERENCE TO RELATED APPLICATION

This application claims the benefit of Korean patent application No. 10-2016-0145174 filed on Nov. 2, 2016, the entire content of which is incorporated herein by reference for all purposes as if fully set forth herein.

BACKGROUND

Field of the Present Disclosure

The present disclosure relates to prevention and treatment for adult diseases caused by respiratory diseases (cough, sputum, rhinitis, bronchitis, asthma and pneumonia) and blood circulation disorders (hypertension, diabetes, dysfunction of each organ, hand and foot pain, and erectile dysfunction).

Specifically, the present invention relates to herbal medicine containing as an effective ingredient a mixture of powders of platycodon grandiflorus and powders of momordica charantia, wherein the powder of platycodon grandiflorus contains powders of leaves and stalks or stem portions of platycodon grandiflorus which have not been used as pharmaceuticals until now.

Discussion of Related Art

Most modern health supplements and medicines are artificial preparations that are basically manufactured based on chemical ingredients. Therefore, there is always a risk of side effects and the like. In addition, such artificial health supplements and medicines are causing various problems such as damage to internal organs during long-term use.

PRIOR ART DOCUMENT

Patent Literature (Patent Document 1) Korean Patent No. 10-1050821
(Patent Document 2) Korean Patent No. 10-1312491
(Patent Document 3) Korean Patent No. 10-0862096

Non-Patent Document (Non-Patent Document 1) A herbal medicine book compilation committee, Revised 2nd edition of Herbal Medicine, Part II, pp. 114.
(Non-Patent Document 2) Jeong Chang Ho, et al, "Chemical composition and antioxidant activity of platycodon grandiflorus leaf and stem', Journal of the Korean Society of Food Science and Nutrition Vol. 35, fifth, Pp. 511-515, 2006.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The present disclosure is to provide prevention and treatment for adult diseases caused by respiratory diseases (cough, sputum, rhinitis, bronchitis, asthma and pneumonia) and blood circulation disorders (hypertension, diabetes, dysfunction of each organ, hand and foot pain, and erectile dysfunction) using herbal medicine containing as an effective ingredient a mixture of powders of platycodon grandiflorus and powders of momordica charantia, wherein the herbal medicine disallows various problems such as damage to internal organs during long-term use.

In one aspect of the present disclosure, there is provided a method for preparing mixture powders of platycodon grandiflorus and momordica charantia, wherein the method includes washing at least one year-old platycodon grandiflorus, and momordica charantia wherein the platycodon grandiflorus includes stem, root, and leaf portions thereof; cutting the washed platycodon grandiflorus and momordica charantia into a predetermined length; hot air-drying the cut platycodon grandiflorus and momordica charantia in a dryer at a temperature exceeding a boiling point of hydrogen cyanide gas; pulverizing the cut and dried platycodon grandiflorus and momordica charantia to prepare platycodon grandiflorus powders and momordica charantia powders; and mixing the platycodon grandiflorus powders and momordica charantia powders at a weight % mixing ratio in a range of 1:0.5 to 1:1.5 to produce the mixture powders of platycodon grandiflorus and momordica charantia.

According to one embodiment, the method may further include adding 3 to 5 wt % roasted salt to the platycodon grandiflorus powders and 3 to 5 wt % roasted salt to the momordica charantia powders.

In one aspect of the present disclosure, there is provided a method a method for preparing a capsule containing therein mixture powders of platycodon grandiflorus and momordica charantia, wherein the method may include washing at least one year-old platycodon grandiflorus, and momordica charantia wherein the platycodon grandiflorus includes stem, root, and leaf portions thereof; cutting the washed platycodon grandiflorus and momordica charantia into a predetermined length; hot air-drying the cut platycodon grandiflorus and momordica charantia in a dryer at a temperature exceeding a boiling point of hydrogen cyanide gas; pulverizing the cut and dried latycodon grandiflorus and momordica charantia to prepare latycodon grandiflorus powders and momordica charantia powders; mixing the platycodon grandiflorus powders and momordica charantia powders at a weight % mixing ratio in a range of 1:0.5 to 1:1.5 to produce the mixture powders of platycodon grandiflorus and momordica charantia; and filling the mixture powders into a gelatin-embodied capsule member.

In one embodiment, in the drying operation, the cut platycodon grandiflorus and momordica charantia are dried for a predetermined time with a hot air of a temperature exceeding the boiling point of the hydrogen cyanide, which is 25.7° C., such that hydrogen cyanide is removed or volatized from the platycodon grandiflorus and momordica charantia.

In one embodiment, the platycodon grandiflorus powders and the momordica charantia powders may be mixed with each other at a mixing ratio by weight of about 1:1.

According to the present invention, the mixture powders of platycodon grandifloras and momordica charantia and, the capsules containing the mixture powders are based on pure natural herbal medicine without any artificial additives, and, thus, have no side effects in the human body, and can be effectively used for symptom improvement and preventive treatment at a relatively small amount due to the synergy effect between platycodon grandifloras and momordica charantia. In addition, the mixture powders may be transparently encapsulated into the capsules so that the mixture powders can be stored for a long period of time, the capsules can be conveniently carried anywhere, anytime, and the user can confirm the abnormality of the contents therein. Further, the capsules can be easily taken and have a low cost.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTIONS

Figure 1:
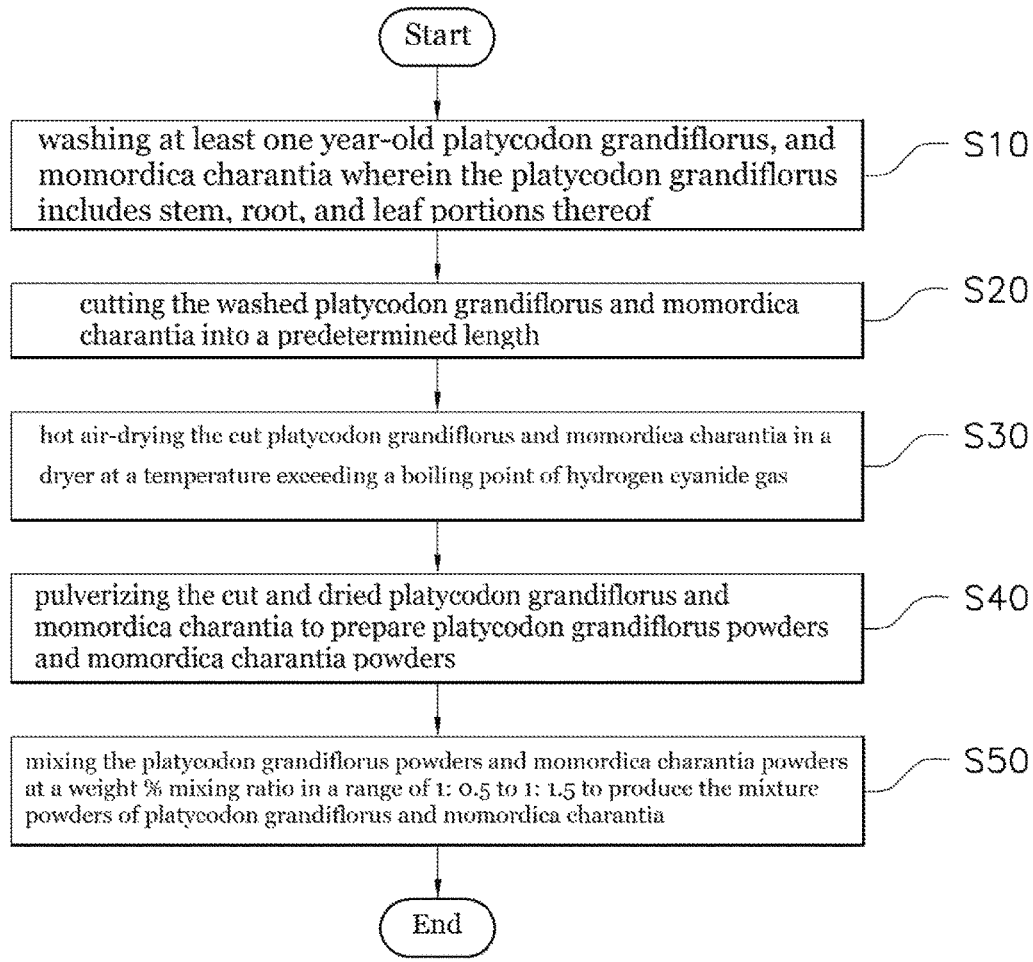
FIG. 1 is a flow chart illustrating an example of a method for producing mixture powders of platycodon grandiflorus and momordica charantia according to the present invention.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure.

Figure 2:
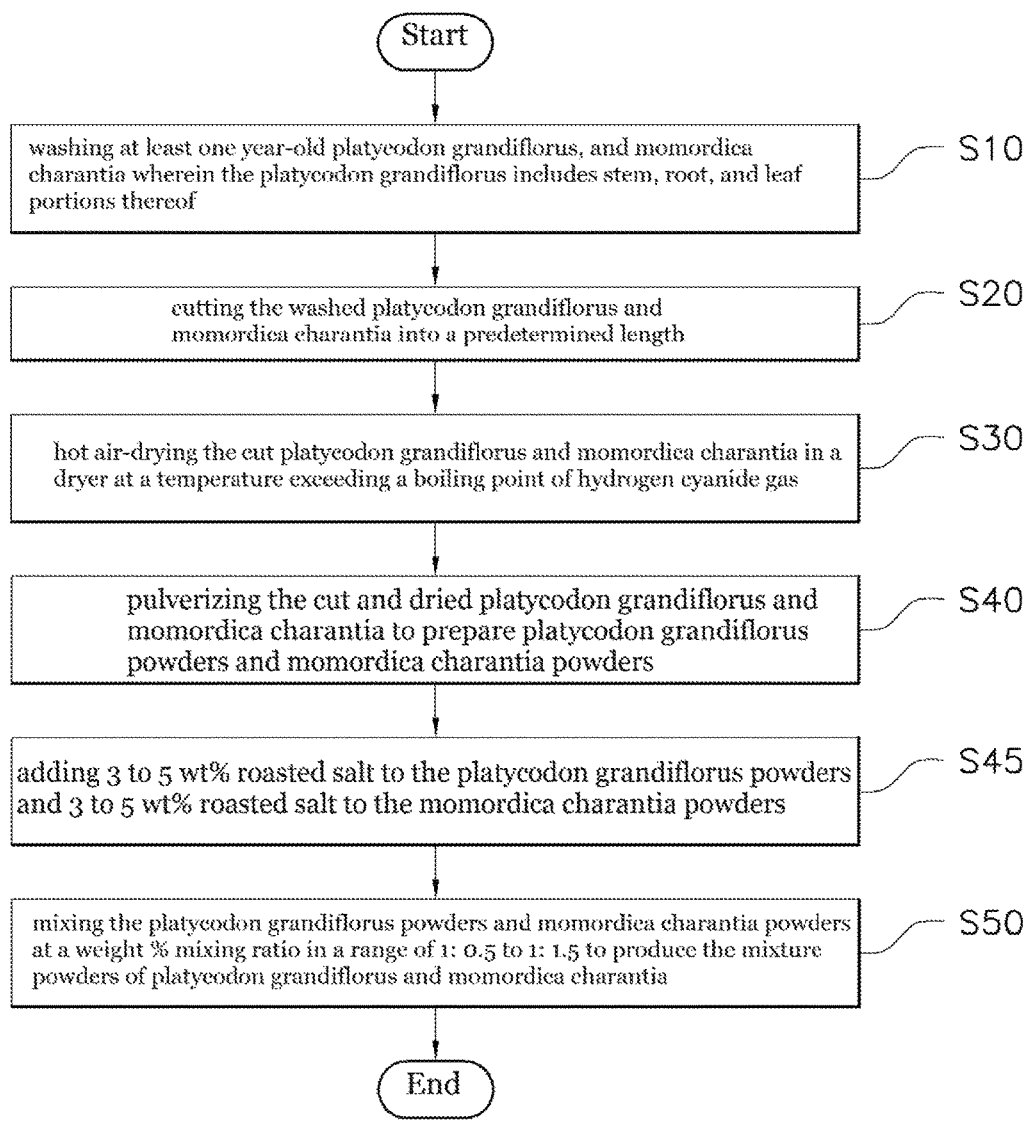
FIG. 2 is a flow chart illustrating another example of a method for producing mixture powders of platycodon grandiflorus and momordica charantia according to the present invention.
Figure 3:
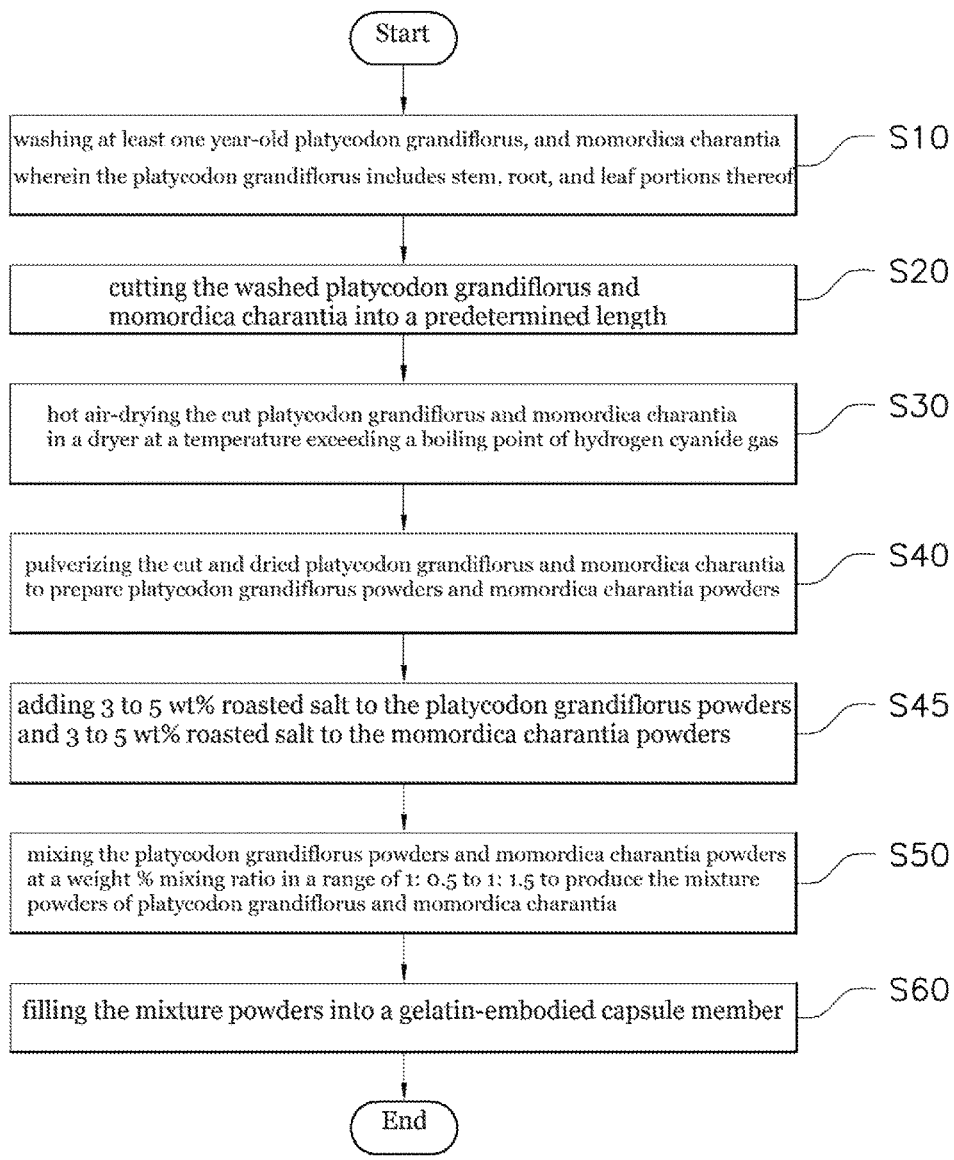
FIG. 3 is a flow chart illustrating a method for preparing capsules comprising mixture powders of platycodon grandiflorus and momordica charantia according to the present invention.

FIG. 1 is a flow chart illustrating an example of a method for producing mixture powders of platycodon grandiflorus and momordica charantia according to the present invention. FIG. 2 is a flow chart illustrating another example of a method for producing mixture powders of platycodon grandiflorus and momordica charantia according to the present invention. FIG. 3 is a flow chart illustrating a method for preparing a capsule comprising mixture powders of platycodon grandiflorus and momordica charantia according to the present invention.

According to the present invention, the mixture powders of platycodon grandifloras and momordica charantia and, the capsules containing the mixture powders are based on pure natural herbal medicine without any artificial additives, and, thus, have no side effects in the human body, and can be effectively used for symptom improvement and preventive treatment at a relatively small amount due to the synergy effect between platycodon grandifloras and momordica charantia. In addition, the mixture powders may be transparently encapsulated into the capsules so that the mixture powders can be stored for a long period of time, the capsules can be conveniently carried anywhere, anytime, and the user can confirm the abnormality of the contents therein. Further, the capsules can be easily taken and have a low cost.

To achieve the above object, the mixture powders of platycodon grandiflorus and momordica charantia according to the present invention may be prepared by pulverizing all of leaves, stems and roots of platycodon grandiflorus and momordica charantia to obtain powers thereof and mixing them together.

In one embodiment, it is also considered to add roasted salt to these mixture powders.

According to the present invention, the capsules surrounding the mixture powders of platycodon grandiflorus and momordica charantia may be prepared by filling the mixture powders described above into a gelatin-embodied capsule member.

Conventionally, only roots of platycodon grandifloras are generally used for medicinal purposes. However, according to the present invention, all of leaves, stems and roots of platycodon grandifloras are used.

According to the present invention, the dry mixture powders of platycodon grandifloras including their leaves, stems and roots, and momordica charantia, and/or capsules containing the above mixture powders, are useful as medicines for the prevention and treatment of adult diseases caused by respiratory diseases and circulatory disorders.

Now, a method for producing mixture powders of platycodon grandiflorus and momordica charantia according to the present invention will be described.

According to one embodiment of the present invention, a method for preparing mixture powders of platycodon grandiflorus and momordica charantia, as shown in FIG. 1, may include washing at least one year-old platycodon grandiflorus, and momordica charantia wherein the platycodon grandiflorus includes stem, root, and leaf portions thereof (S10); cutting the washed platycodon grandiflorus and momordica charantia into a predetermined length (S20); hot air-drying the cut platycodon grandiflorus and momordica charantia in a dryer at a temperature exceeding a boiling point of hydrogen cyanide gas (S30); pulverizing the cut and dried platycodon grandiflorus and momordica charantia to prepare platycodon grandiflorus powders and momordica charantia powders (S40); and mixing the platycodon grandiflorus powders and momordica charantia powders at a weight % mixing ratio in a range of 1:0.5 to 1:1.5 to produce the mixture powders of platycodon grandiflorus and momordica charantia (S50).

According to the present invention, the method may further include, between the operation (S40) and the operation (S50), an operation (S45) of adding 3 to 5 wt % roasted salt to the platycodon grandiflorus powders and 3 to 5 wt % roasted salt to the momordica charantia powders.

According to the present invention, there is provided a method for preparing capsules comprising mixture powders of platycodon grandiflorus and momordica charantia, wherein the method may include washing at least one year-old platycodon grandiflorus, and momordica charantia wherein the platycodon grandiflorus includes stem, root, and leaf portions thereof (S10); cutting the washed platycodon grandiflorus and momordica charantia into a predetermined length (S20); hot air-drying the cut platycodon grandiflorus and momordica charantia in a dryer at a temperature exceeding a boiling point of hydrogen cyanide gas (S30); pulverizing the cut and dried platycodon grandiflorus and momordica charantia to prepare platycodon grandiflorus powders and momordica charantia powders (S40); mixing the platycodon grandiflorus powders and momordica charantia powders at a weight % mixing ratio in a range of 1:0.5 to 1:1.5 to produce the mixture powders of platycodon grandiflorus and momordica charantia (S50); and filling the mixture powders into a gelatin-embodied capsule member (S60).

The method for preparing the mixture powders of platycodon grandiflorus and momordica charantia according to the present invention comprises the washing operation (S10), the cutting operation (S20), the drying operation (S30), the pulverizing operation (S40) and the mixing operation S50. Additionally, as in FIGS. 2 and 3, the salt addition operation (S45) and/or the encapsulation operation (S60) may be added thereto.

First, for the washing operation (S10), one year old or perennial platycodon grandiflorus may be harvested. In this connection, all of the root, leaf and stem portions are harvested. In this regard, native species of platycodon grandiflorus may be harvested.

Then, regarding mortordica charantia, a native momordica charantia may be used. Slightly less ripe green momordica charantia may be harvested.

The harvested platycodon grandiflorus and momordica charantia are washed clean.

Thereafter, in the cutting operation (S20), the washed platycodon grandiflorus is cut to a predetermined size to be inserted into the dryer. Then, the washed momordica charantia is prepared by slicing it.

Next, in the drying operation (S30), the cut platycodon grandiflorus and momordica charantia are dried for a predetermined time with a hot air of about 60 degrees C. The predetermined time is proportional to the amounts of platycodon grandiflorus and momordica charantia to be dried.

In the drying operation (S30), the cut platycodon grandiflorus and momordica charantia are dried for a predetermined time with a hot air of about 60 degrees C. such that toxic harmful to the human body which is contained in all blue plant species. In particular, the cut platycodon grandiflorus and momordica charantia are dried for a predetermined time with a hot air of about 60 degrees C. such that hydrogen cyanide is removed or volatized from the platycodon grandiflorus and momordica charantia. In this connection, the cut platycodon grandiflorus and momordica charantia are dried at a temperature exceeding the boiling point of the hydrogen cyanide, which is 25.7° C.

In one embodiment, about 60 degrees C. may be merely one example of the temperature exceeding the boiling point of the hydrogen cyanide. The present invention may not be limited thereto.

Then, in the pulverizing operation (S40), the dried platycodon grandiflorus is pulverized using a pulverization machine including cutting blades rotating at a high speed. Further, in the pulverizing operation (S40), the dried momordica charantia is pulverized using a pulverization machine including cutting blades rotating at a high speed.

In this connection, in the pulverizing operation (S40), the pulverizations of the platycodon grandifloras and momordica charantia may be performed in the pulverization machine individually. This is because the platycodon grandiflorus powders and momordica charantia powders are mixed at an accurate quantitative mixing ratio at a subsequent operation.

Then, the pulverized platycodon grandiflorus is filtered with a filter having a predetermined size to remove non-pulverized woody parts. This results in pale green platycodon grandiflorus powders. The pulverized momordica charantia is also filtered by a filter of a predetermined size such that surfaces of seeds as not filtered are removed. This results in golden momordica charantia powders.

As shown in FIG. 2, in the salt addition operation (S45) which may be selectively performed, a predetermined amount of roasted salt (for example, bamboo salt) powders is added to the platycodon grandiflorus powders, to obtain a first mixture. The predetermined amount may be preferably about 3 to 5 wt %. Then, the first mixture is evenly mixed using a mixing tool.

Further, in the salt addition operation (S45) which may be selectively performed, a predetermined amount of roasted salt (for example, bamboo salt) powders is added to the momordica charantia powders, to obtain a second mixture. The predetermined amount may be preferably about 3 to 5 wt %. Then, the second mixture is evenly mixed using a mixing tool.

In this salt addition operation (S45), the roasted salt (for example, considering economics, three bamboo salt additions) is added for a following reason: Even after the hot air drying, a small amount of moisture may remain in the finished product. The moisture may cause corruption when the finished product is stored for a long period of time.

Therefore, in adding the salt, the moisture may be absorbed by the salt powder. At the same time, the sealed state is maintained by the capsule packing, so that the final product has an excellent function that does not corrupt even if stored for a long period of time.

The operation of adding the roasted salt may be performed at the same time as after the mixing operation (S50) to be described later. However, by adding the roasted salt to the platycodon grandiflorus powder or momordica charantia powder as soon as possible, the platycodon grandiflorus powder or momordica charantia powder may be prevented from corruption. Therefore, it is preferable that the salt addition operation (S45) is performed before the mixing operation (S50).

Next, in the mixing operation (S50), the platycodon grandiflorus powders and the momordica charantia powders, each having the roasted salt added thereto, are mixed at a weight mixing ratio in a range of about 1:0.5 to 1:1.5. This mixture is mixed evenly using a mixer to complete the mixture powders of the platycodon grandiflorus and momordica charantia. The final product may have a combination of golden color and pale green.

In one embodiment, the platycodon grandiflorus powders and the momordica charantia powders may be mixed with each other at a mixing ratio by weight of about 1:1. In this way, the mixture powders of the platycodon grandiflorus and momordica charantia according to the present invention may be prepared.

Then, in one embodiment as shown in FIG. 3, in the encapsulation operation (S60) that may be selectively performed, the mixture powders of the platycodon grandiflorus and momordica charantia prepared as described above are filled in a transparent capsule member using a capsule filling machine to encapsulate the mixture powders of the platycodon grandiflorus and momordica charantia.

In this connection, the capsule member may be formed of natural gelatin (a dye-free transparent material) made from animal (for example, cow) bones or leather.

Via this encapsulation operation (S60), the capsules containing the mixture powders of platycodon grandiflorus and momordica charantia according to the present invention may be produced.

The root portion of platycodon grandiflorus may be effective for respiratory diseases. Furthermore, the platycodon grandiflorus may have antioxidant activity by various components contained in leaf and stem portions of platycodon grandiflorus. Thus, according to the present invention, by using all of the root, stems and leaf portions of platycodon grandiflorus, an enhanced pharmaceutical effect may be exhibited.

Momordica charantia may be useful for vascular diseases such as diabetes, hypertension and the like. When platycodon grandiflorus and momordica charantia are combined with each other in the mixture powder form, the pharmaceutical effect of this mixture becomes much larger than when platycodon grandiflorus and momordica charantia are individually present. In order to identify the pharmaceutical effect, the blood circulation system of the human body should be understood first.

The blood circulation in the human body may be classified into the pulmonary circulation and the systemic circulation. To maintain a healthy human body, blood must be supplied with fresh oxygen from the lungs of humans and be circulated smoothly to every portion of the body along with nutrients.

In this regard, it is platycodon grandiflorus that has a positive effect on the pulmonary circulation, while, it is momordica charantia which has a positive effect on the systemic circulation.

When respiratory illness causes difficulty in normal breathing, it causes obstruction of the pulmonary circulation. At this time, the platycodon grandiflorus may have antitussive and expectorant action to remove respiratory disturbance, thereby regenerating fresh blood. When the blood flow is improved due to the vascular expansion performance of the momordica charantia, various organs and parts of the human body will have normal functions. The mixture of the platycodon grandiflorus and momordica charantia has a synergistic effect and thus has a positive effect on the lung.

The effect of momordica charantia on the systemic cycle will be explained in more detail as follows. Considering the production process of nitrogen monoxide (NO) in the epithelial cells of the blood vessels, the production of nitrogen monoxide is reduced when a person becomes older (mainly after 40 years of age), resulting in various disorders. Momordica charantia contains a large amount of cytotrin, which increases the amount of nitrogen monoxide produced, thereby expanding blood vessels and improving blood flow.

Erectile dysfunction due to blood flow disorders can also be improved by artificially delaying the increase or decrease of nitrogen monoxide production. Thus, the present invention has been demonstrated to act as erectile dysfunction medicines.

Experimental examples of the action and effects of the present invention are as follows: As a result of a person having rhinitis, bronchial inflammation and lung inflammation taking the capsules according to the present invention continuously in a dose of about two per day (about 0.4 g per one capsule), the rhinitis, bronchial inflammation, and lung inflammation were removed from the patient. One patient suffered from the bronchial inflammation and had severe illnesses (blood pressure rapid increase, pulse rate rapid increase, etc.) such as those caused by adverse reactions resulting from having artificial treatment chemical and was carried on 119 ambulances to be taken to the emergency room. This patient has taken the capsules according to the present invention continuously and thus the bronchial inflammation of the patient has been remedied.

In addition, many respiratory diseases have been cured by taking the capsules according to the present invention. In addition, it was recommended to continue taking the capsules. In addition, patients suffering from a blood circulation disorder (chronic fatigue, limp, erectile dysfunction, etc.) have been remedied by taking the capsules according to the present invention.

The mixture powders according to the present invention are pure natural plant products which are also used for edible purposes, so that they have no side effects and can be used in a small dose (about 0.4 g, or 2 to 3 capsules) on a daily basis.

In addition, the capsule member in accordance with the present invention is made of natural gelatin (a transparent material containing no pigment) made of animal (for example, cow) bone or leather, which is a substance used as blood nutrients in an oriental medicine for an inherent weakness such as anemia. This is harmless to the human body. This helps to increase hemoglobin and red blood cells.

The mixture powders of the momordica charantia and platycodon grandiflorus including the leaves, stems and roots thereof according to the present invention showed a synergistic effect for the prevention and treatment of adult diseases caused by various respiratory diseases and blood circulation disorders. This synergistic effect is not exerted when the platycodon grandiflorus and the above-mentioned momordica charantia are present individually.

In particular, when the content of platycodon grandiflorus and the content of momordica charantia is about 1:1, a remarkable synergistic effect is obtained for the prevention and treatment. Further, it is possible to replace conventional preventive and therapeutic agents with the capsule containing the mixture powders of the momordica charantia and platycodon grandifloras at a low cost.

It is to be understood that while the present disclosure has been particularly shown and described with reference to the exemplary embodiments thereof, the disclosure is not limited to the disclosed exemplary embodiments. On the contrary, it will be understood by those skilled in the art that various modifications may be made without departing from the spirit and scope of the present disclosure.

It is understood by those skilled in the art that various variants and alternatives may be selected in the present disclosure without departing from the spirit or scope of the present disclosure. Accordingly, it is intended that the present disclosure covers the modifications and variations when they come within the scope of the appended claims and their equivalents.

The above description is not to be taken in a limiting sense, but is made merely for the purpose of describing the general principles of exemplary embodiments, and many additional embodiments of this disclosure are possible. It is understood that no limitation of the scope of the disclosure is thereby intended. The scope of the disclosure should be determined with reference to the Claims. Reference throughout this specification to "one embodiment," "an embodiment," or similar language means that a particular feature, structure, or characteristic that is described in connection with the embodiment is included in at least one embodiment of the present disclosure. Thus, appearances of the phrases "in one embodiment," "in an embodiment," and similar language throughout this specification may, but do not necessarily, all refer to the same embodiment.

What is claimed is:

1. A method for preparing mixture powders of platycodon grandiflorus and momordica charantia, wherein the method includes:
    washing at least one year-old platycodon grandiflorus, and momordica charantia wherein the platycodon grandiflorus includes stem, root, and leaf portions thereof;
    cutting the washed platycodon grandiflorus and momordica charantia into a predetermined length;
    hot air-drying the cut platycodon grandiflorus and momordica charantia in a dryer at a temperature exceeding a boiling point of hydrogen cyanide gas to remove hydrogen cyanide therefrom, wherein the boiling point is 27.5 degree C.;
    pulverizing the cut and dried platycodon grandiflorus and momordica charantia to prepare platycodon grandiflorus powders and momordica charantia powders; and
    mixing the platycodon grandiflorus powders and momordica charantia powders at a weight % mixing ratio in a range of 1:0.5 to 1:1.5 to produce the mixture powders of platycodon grandiflorus and momordica charantia.

2. The method of claim 1, further comprising filling the mixture powders into a capsule made of gelatin to encapsulate the mixture powders.

* * * * *